United States Patent [19]

Doerpinghaus et al.

[11] Patent Number: 5,419,815
[45] Date of Patent: May 30, 1995

[54] PROCESS FOR PURIFYING FATTY ACID AMIDES

[75] Inventors: Norbert Doerpinghaus, Kriftel; Siegbert Rittner, Moeferlden-Walldorf, both of Germany

[73] Assignee: Hoechst AG, Frankfurt, Germany

[21] Appl. No.: 105,600

[22] Filed: Aug. 12, 1993

[30] Foreign Application Priority Data

Aug. 15, 1992 [DE] Germany .................. 42 27 051.0

[51] Int. Cl.⁶ .............................................. B01D 3/34
[52] U.S. Cl. ........................................ 203/6; 203/14; 203/36; 203/37; 203/38; 203/72; 203/88; 203/89; 203/91; 554/70
[58] Field of Search .............. 203/33, 36, 37, 38, 203/72, 88, 89, 91, 6, 14; 554/70

[56] References Cited

U.S. PATENT DOCUMENTS

| | | | |
|---|---|---|---|
| 3,276,973 | 10/1966 | Burmaster et al. | 203/37 |
| 3,373,174 | 3/1968 | Hammerberg et al. | 260/404 |
| 3,660,248 | 5/1972 | Tsao | 203/37 |
| 3,920,523 | 11/1975 | Lichtenwalter et al. | |

FOREIGN PATENT DOCUMENTS

| | | |
|---|---|---|
| 1459655 | 10/1966 | France . |
| 1593658 | 10/1970 | Germany . |
| 2355856 | 5/1974 | Germany . |
| 46/10533 | 3/1971 | Japan . |
| 1160695 | 8/1969 | United Kingdom .................. 554/70 |
| 1433156 | 4/1976 | United Kingdom . |

OTHER PUBLICATIONS

Derwent Abstract of JP 48 040 330, Week 7349, AN 73-75607U.
Derwent Abstract of JP 46 010 533, Week 7111, AN 71-19942S.

*Primary Examiner*—Wilbur Bascomb, Jr.
*Attorney, Agent, or Firm*—Connolly and Hutz

[57] ABSTRACT

The present invention relates to a process for purifying fatty acid amides, which contains the following process steps:
  neutralization of the fatty acid by addition of an aqueous alkaline solution and
  subsequent distillation of the neutralized mixture.

19 Claims, No Drawings

PROCESS FOR PURIFYING FATTY ACID AMIDES

DESCRIPTION

Process for Purifying Fatty Acid Amides

Fatty acid amides are prepared by the ammonolysis of fatty acid esters or by the dehydrating amidation of fatty acids, their main impurities generally being free fatty acids and nitriles and impurities present in the starting material.

For some time there has been a need for purified fatty acid amides which contain as small as possible a proportion of free fatty acids and nitriles, do not possess a sticky or greasy consistency, show little discoloration (iodine or Gardner color number) and are free of any rancid smell.

JP-B-46/105 33 (Application number 43/36844, Applicant: Nitto Kagaku Kogyo Kabushiki Kaisha) gives a process for purifying higher fatty acid amides, in which the fatty acid amides are subjected to a vacuum distillation in the presence of tertiary sodium phosphate or tertiary potassium phosphate. In this process fatty acid amides are obtained, in yields of from 90 to 97%, which have a nitrile content of from 0.7 to 3% by weight, having started with a nitrile content of 4% by weight. The coloration of the crude amide used is from 6 to 7 degrees (Gardner scale). Disadvantages of this process are that only crude amides with a low content of coloring impurities can be used and that the products have too high a nitrile content.

U.S. Pat. No. 3,920,523 discloses a process for purifying neutralized fatty acid amides having from 14 to 22 carbon atoms in the fatty acid, which contain free fatty acids as the impurity and in which process the fatty acid amides are subjected to a molecular distillation at reduced pressure. The crude or unpurified fatty acid amides used generally have a content of from 2 to 7% by weight of unreacted fatty acid, based on the reaction mixture, and from 0.5 to 1% by weight of nitrile. A preferred embodiment of the process comprises the neutralization of a reaction mixture containing from 2 to 6% by weight of oleic acid with an alcoholic solution of an alkali metal hydroxide or sodium methoxide in methanol using an excess of from 6 to 20% of the base. After neutralization the alcoholic solution is removed by distillation and the neutralized mixture subjected to molecular distillation. The free oleic acid content of the distillate is from 0.06 to 0.6% by weight, while the free oleic acid content of the crude amide is 3.4% by weight. The yield of distillate is from 70 to 93.5% by weight. The nitrile content remains unchanged at from 0.5 to 1% by weight, and the colored impurities of the starting material are present in small amounts and produce a coloration of from 4 to 8 degrees on the Gardner scale. The vacuum distillation in the process leads to a reduction in the discoloration of the amides to less than 1 degree (Gardner scale).

Disadvantages of this process are that the nitrile content cannot be reduced, and that only fatty acid amides having a relatively low and closely limited free oleic acid content and a low content of coloring impurities can be used. Furthermore, the use of lower alcohols as solvents necessitates a two-stage distillation. In addition, the waste air problems with organic solvents must be controlled.

An object of the invention is to make available a process in which even fatty acid amides with a free oleic acid content of above 6% by weight can be used, the distillate contains less than 0.4% by weight of nitrile and less than 0.5% by weight of free oleic acid, in which a two-stage distillation is not absolutely necessary and very dark fatty acid amides with a high content of coloring substances (Gardner color number from 15 to 18) can be purified.

The present invention provides a process for purifying fatty acid amides in admixture with free fatty acids, with or without further impurities, comprising the process steps of:

neutralizing the fatty acid by addition of an aqueous alkaline solution and subsequently distilling the neutralized mixture.

The crude or unpurified fatty acid amide used is generally a technical-grade $C_{14}$–$C_{22}$ saturated, unsaturated or polyunsaturated fatty acid amide, preferably oleamide, which comprises a mixture of fatty acid amides, preferably oleamide, but may also contain some saturated and unsaturated $C_{14}$–$C_{16}$ amides and $C_{18}$ polyunsaturated amides. In addition, other fatty acid amides, such as erucamide and stearamide, can be used. The oleamides and stearamides in general contain some $C_{16}$ fatty acid amides. The amides can be simply prepared on an economic scale by reaction of the corresponding fatty acids with ammonia. The reaction mixture obtained has a nitrile content of less than 1% by weight, preferably from 0.1 to 0.5% by weight. The fatty acid is generally present as up to 15% by weight, preferably less than 10% by weight, particularly preferably from 2 to 6% by weight, of the crude amide mixture. In addition, varying amounts of coloring substances may also be present. These are generally simply described as colorants. In the mixtures used they are present in such concentration as to produce a color of greater than 18 degrees on the Gardner scale in the fatty acid amide to be purified. The water content of the fatty acid amides to be purified is usually below 5% by weight. Furthermore small amounts, less than 1% by weight, of concomitants such as esters, ketones and/or hydrocarbons may be present. A crude amide reaction mixture of this composition is most suitable for the process for reducing the acid content according to this invention. The process normally leads to a reduction in the discoloration of the amide to 1 degree (Gardner scale) with the two-stage distillation, and to from 2 to 6 degrees with the single-stage distillation. An increase in the nitrile content over that in the starting material can not be detected.

In carrying out the process of the invention the crude amide mixture, which can contain up to 15% by weight of oleic acid, is first neutralized with an aqueous solution of an alkali metal and/or alkaline earth metal hydroxide, such as sodium hydroxide or calcium hydroxide. The type of base employed for neutralization is not critical. True, the experiments were restricted to inorganic bases, but other bases, such as organic quaternary ammonium hydroxides, for example tetraethylammonium hydroxide, tetramethylammonium hydroxide, benzyltrimethylammonium hydroxide and benzyltriethylammonium hydroxide, can also be used.

To neutralize the oleic acid in the crude amide mixture the aqueous alkaline solution should be as concentrated as possible to minimize the amount of water to be subsequently separated off. At the same time it is desirable to make the aqueous alkali-treated crude amide mixture of a pumpable consistency, so that it can subsequently be introduced into a suitable distillation apparatus. Depending on the content of free fatty acid and on the chosen excess of alkali solution, a from 5 to 60% by weight strength aqueous alkaline solution is used and the weight ratio of the crude amide mixture to aqueous alkali is from 10:0.5 to 3, preferably 10:1. It has become evident that it is advantageous to use an excess of aqueous alkaline solution. The excess of aqueous alkaline solution is generally from 0.2 to 1.8 mol, preferably 1.0 mol, based on the oleic acid content. Although a sufficient purity can already be achieved with a 0.2 molar excess of aqueous alkaline solution, a molar excess has proved best in practice.

In the neutralization of the fatty acid the crude amide mixture is melted, admixed with aqueous alkali and mixed with stirring at from 80° to 100° C. In addition, the melt can be admixed with about 0.05% by weight of an antioxidant, such as sodium hypophosphite, hydroquinone or 2,6-di-tert-butyl-4-methylphenol.

The neutralization of the oleic acid is followed by the removal of the water by distillation, and the distillative extraction of the fatty acid amide.

The removal of the water and the distillative extraction of the fatty acid amide is possible in a single-stage or a two-stage process. The single-stage distillation is advantageous if the acid content of the crude amide to be purified is from 3 to 4% by weight and the NaOH-excess does not exceed from 1.0 to 1.2 mol. With a higher acid content or NaOH-excess a two-stage distillation is to be recommended.

In the single-stage process water and fatty acid amides are simultaneously subjected to distillation. The distillation is preferably carried out in a thin film evaporator, for example the ®Normag-Rotafilm apparatus (System Canzler), from which the fatty acid amide distills off at the top simultaneously with the water, which is collected in the cold trap.

In the two-stage process water and fatty acid amide are successively subjected to distillation. The distillation preferably proceeds in a thin film evaporator, in which the water is first distilled off in a low vacuum (from 300 to 400 mbar) at a temperature of from 120° to 140° C., and the organic components are collected as a concentrate at the bottom. Subsequently the concentrate is distilled in a high vacuum (from 0.01 to 0.1 mbar), producing the purified oleamide as the top phase. As a protection against oxidation, the distillate is admixed with about 0.05% by weight of an antioxidant.

In the two-stage process it is advantageous to arrange two distillation apparatus in series, in which case the arrangement may comprise two thin film evaporators or one thin film evaporator, in which the water is distilled off, and one shortpath evaporator, for example a ®Normag-Rotafilm shortpath evaporator, in which the fatty acid amide is distilled off.

When highly impure products (acid content above 4% by weight, Gardner number greater than 6) are employed, the use of an arrangement in series of two thin film evaporators has proved suitable.

The fatty acid amide obtained in this way is produced in high yield and purity with a low nitrile content. The color of the distillate on the Gardner scale is from 2 to 6 degrees with the single-stage distillation, or 1 degree with the two-stage distillation.

Because of the low nitrile content the product possesses an advantageously solid and hard consistency and can be prepared in ready-to-use form corresponding to the sales requirements as a high-value micro-granulated product, as flakes or as a ground powder, but also simply as "cast product" in molds.

Such an oleamide is preferred for application as a mold release agent, a lubricant in plastic film production, a water repellent and as a raw material for cosmetics production.

An advantage of the process is that a crude amide mixture with a high content of free fatty acid and coloring impurities can be used. In the neutralization step, water is used to dissolve the hydroxides, whereby the waste air purification customary for organic solvents becomes unnecessary. For the distillative purification either a thin film or a flash evaporator can be used. A molecular distillation unit as indicated in DE-A-23 55 856 is not absolutely necessary.

The process of the invention is explained by the following examples:

EXAMPLE 1

(Single-Stage Distillation)

Experiment A:

200 g of crude oleamide are melted and admixed with an aqueous sodium hydroxide solution, containing 0.96 g of solid NaOH in 20 g of water. The amount of alkali is sufficient to neutralize the total free acid in the crude amide and to give an additional 0.2 molar excess. The crude amide mixture is, after addition of 0.1 g of antioxidant, mixed well for 1 hour at 100° C.

The crude amide mixture used has the following composition:

| | |
|---|---|
| Primary oleamide: | 86.7% |
| Oleic acid and salts thereof: | 2.8% |
| Oleonitrile: | <0.5% |
| Water: | 4.6% |
| Sum of ester, ketone and hydrocarbon: | <1.5% |
| Other impurities: | 3.6% |
| Solidification point: | 70.4° C. |
| Gardner color number: | >18 degrees |

The neutralized alkali-containing crude amide melt is introduced into a laboratory thin film evaporator (System Canzler, 0.03 m² evaporator surface) and subjected to vacuum distillation at an evaporator surface temperature of 190° C. and a pressure of 0.01 mbar. The oleamide is collected at 90° C. and reacted with antioxidant. The feed is maintained at 100° C.

In the same manner as in Experiment A, 200 g of crude oleamide are treated with 1.60 g (B) and 1.76 g (C, D) of solid NaOH dissolved in 20 g of water, and subsequently distilled in the thin film evaporator.

Results of the oleamide purification after the distillation are given in Table 1.

TABLE 1

| | Experiment | | | |
|---|---|---|---|---|
| Component/parameter | A | B | C | D |
| Oleamide % | 96.7 | 97.7 | 97.5 | 98.7 |
| Oleic acid % | 1.8 | 0.5 | 0.3 | 0.1 |
| Oleonitrile % | 0.1 | 0.1 | 0.1 | 0.1 |
| Ester, ketone and hydrocarbon % | <0.3 | <0.3 | <0.3 | <0.3 |
| Melting point °C. | 70.0 | 70.0 | 70.0 | 71.0 |
| NaOH-excess mol | 0.2 | 1.0 | 1.2 | 1.2 |
| Yield % | 86.4 | 89.2 | 75.4 | 75.8 |

In experiment D the purification step, comprising neutralization and distillation, was repeated once. Input was experiment C. The Gardner color number of the distillate is from 2 to 6 degrees.

EXAMPLE 2

(Two-Stage Distillation)

200 g of crude oleamide are neutralized with 8.8 g solid NaOH dissolved in 20 g of water (1.8 molar excess) as described in Example 1.

The crude amide mixture used has the following composition:

| | |
|---|---|
| Primary oleamide: | 87.1% |
| Oleic acid and salts thereof: | 11.1% |
| Oleonitrile: | 0.1% |
| Water: | 1.2% |
| Sum of ester, ketone and hydrocarbon: | <0.3% |
| Solidification point: | 63.7° C. |
| Gardner color number: | >18 degrees |

In a first evaporator step the water is separated off in a thin film evaporator at 140° C. and a pressure of 350 mbar.

Subsequently the dewatered crude amide melt is reintroduced into the evaporator. The amide distillation proceeds at an evaporator surface temperature of 215° C. and a pressure of 0.01 mbar. The feed is maintained at 140° C. and the amide condensed at 90° C. The characteristics of the purified amide are given in Table 2.

TABLE 2

| Component/parameter | Example 2 |
|---|---|
| Oleamide % | 98.9 |
| Oleic acid % | 1.1 |
| Oleonitrile % | 0.1 |
| Ester, ketone and hydrocarbon % | <0.3 |
| Melting point °C. | 72.0 |
| Iodine color number | 1 |
| Gardner color number | 1 |
| APHA color number | 123 |
| NaOH-excess mol | 1.8 |
| Yield % | 71.1 |

What is claimed is:

1. A process for purifying fatty acid amides, comprising taking a crude fatty acid amide mixture which comprises a fatty acid amide and a fatty acid and subjecting said mixture to the process steps of
   neutralizing the mixture by the addition of an aqueous alkali solution, and
   subsequently distilling the neutralized mixture in order to obtain purified fatty acid amide wherein the amide mixture to be purified is in a weight ratio to aqueous alkali from 10:0.5 to 3.

2. The process as claimed in claim 1, wherein the aqueous solution of an alkali metal hydroxide and/or of an alkaline earth metal hydroxide is used.

3. The process as claimed in claim 1, wherein a from 5 to 60% by weight strength aqueous alkali solution is used.

4. The process as claimed in claim 1, wherein the aqueous alkali solution is used in a molar excess.

5. The process as claimed in claim 1, wherein the neutralization is effected by adding the aqueous alkali solution to a melt containing the crude fatty acid amide mixture and subsequently stirring at a temperature of from 80° to 100° C.

6. The process as claimed in claim 5, wherein the melt is admixed with an antioxidant.

7. The process as claimed in claim 1, wherein the distillation is effected in a single stage.

8. The process as claimed in claim 1, wherein the distillation is effected in two stages.

9. The process as claimed in claim 1, wherein the aqueous solution of sodium hydroxide is used.

10. The process as claimed in claim 1, wherein the aqueous alkali solution is used in an excess from 0.2 to 1.8 mol, based on the fatty acid content.

11. The process as claimed in claim 1, wherein the distillation is effected in a single stage using a thin film evaporator.

12. The process as claimed in claim 1, wherein the distillation is effected in two stages with an arrangement in series wherein the residue flows in series.

13. The process as claimed in claim 12, wherein the distillation is effected in two stages with an arrangement in series in which case the arrangement comprise two thin film evaporators in series or one thin film evaporator and one flash evaporator.

14. A process for purifying fatty acid amides, comprising taking a crude fatty acid amide mixture which comprises a fatty acid amide and a fatty acid and subjecting said mixture to the process steps of
   neutralizing said mixture by addition of an aqueous alkali solution to a melt containing the crude fatty acid amide mixture,
   adding an antioxidant to said mixture,
   subsequently stirring said mixture admixed with said antioxidant at a temperature of from 80° to 100° C., and
   subsequently distilling the neutralized mixture in order to obtain a purified fatty acid amide.

15. A process for purifying fatty acid amides, comprising taking a crude fatty acid amide mixture which comprises a fatty acid amide and a fatty acid and subjecting said mixture to the process steps of
   neutralizing the mixture by the addition of an aqueous alkali solution,
   subsequently distilling the neutralized mixture in order to obtain purified fatty acid amide wherein the crude fatty acid amide mixture to be purified is in a weight ratio to aqueous alkali from 10:0.5 to 3, wherein the purified fatty acid amide has a nitrile content of less than 1% by weight and the fatty acid is present in an amount up to 15% by weight of the crude mixture.

16. The process as claimed in claim 15, wherein the nitrile content is from 0.1 to 0.5% by weight and the fatty acid is present from 2 to 6% by weight of the crude mixture.

17. The process as claimed in claim 1, wherein the crude mixture further comprises oleic acid and the aqueous alkali solution is present in an amount from 0.2 to 1.8 mol based on the oleic acid content in the crude mixture.

18. The process as claimed in claim 8, wherein the crude fatty acid amide mixture to be purified has an acid content greater than 4% by weight or the aqueous alkali solution used contains greater than 1.2 mols of NaOH.

19. The process as claimed in claim 7, wherein the acid content of the crude fatty acid amide to be purified is from 3 to 4% by weight and the aqueous alkali solution does not exceed from 1.0 to 1.2 mol.

* * * * *